United States Patent [19]

Le Floc'H et al.

[11] Patent Number: 5,052,227

[45] Date of Patent: Oct. 1, 1991

[54] DEVICE AND PROBE FOR MEASURING THE VARIATION OF DISTANCE BETWEEN THE TWO FACES OF A LAYER OF MATERIAL BY MEANS OF ULTRASOUNDS

[75] Inventors: Christian M. Le Floc'H, Blanquefort; François Perrot, Merignac, both of France

[73] Assignee: Societe Nationale Industrielle, Paris, France

[21] Appl. No.: 612,208

[22] Filed: Nov. 13, 1990

[30] Foreign Application Priority Data

Nov. 14, 1989 [FR] France ................. 89 14927

[51] Int. Cl.$^5$ ............................................. G02N 9/24
[52] U.S. Cl. ........................................ 73/644; 73/597; 73/624; 73/627
[58] Field of Search ............... 73/644, 597, 616, 620, 73/624, 627

[56] References Cited

U.S. PATENT DOCUMENTS

| 4,287,769 | 9/1981 | Buckley . | |
| 4,510,812 | 4/1985 | Feng | 73/644 |
| 4,658,648 | 4/1987 | Roddeck | 73/597 |
| 4,669,310 | 6/1987 | Lester | 73/597 |
| 4,672,851 | 6/1987 | Blessing et al. | 73/597 |

FOREIGN PATENT DOCUMENTS 2351420 12/1977 France .
2476831 8/1981 France .

Primary Examiner—Hezron E. Williams
Assistant Examiner—William Francos
Attorney, Agent, or Firm—Marshall, O'Toole, Gerstein, Murray & Bicknell

[57] ABSTRACT

A device is disclosed for measuring the variation of the distance separating the two faces of a layer of solid material by means of ultrasounds, comprising:
  a generator generating a first alternating electric signal,
  an electroacoustic transmitting transducer,
  first coupling means for applying the ultrasonic wave to said layer of material,
  an electroacoustic receiving transducer,
  second coupling means for applying said ultrasonic wave to said electroacoustic receiving transducer,
  means for continuously measuring the variation of the phase-shift of the electric signal emitted by the receiving transducer with respect to said first alternating electric signal, and
  computing means for deriving said distance variation from said phase-shift variation, wherein:
  said electroacoustic transmitting and receiving transducer, as well as said first and second coupling means are disposed on the same side of said layer of material, and
  said first and second coupling means are solid ultrasonic wave-guides.

10 Claims, 2 Drawing Sheets

DEVICE AND PROBE FOR MEASURING THE VARIATION OF DISTANCE BETWEEN THE TWO FACES OF A LAYER OF MATERIAL BY MEANS OF ULTRASOUNDS

BACKGROUND OF THE INVENTION

1. Field of the Invention

The present invention relates to a device and probe for measuring the variation of distance between the two faces of a layer of material by means of ultrasounds.

The principle of known devices of this type is generally based on the timing of pulses, i.e. the time taken by ultrasonic pulses to travel through said layer of material is measured and the thickness thereof is derived therefrom by multiplying this travel time by the speed of said ultrasonic pulses in the material. These known devices are not very accurate and have poor resolution, because of the uncertainty with which the beginning of each pulse is known.

2. Description of the Prior art

In order to improve such known devices, radar or sonar techniques have been applied thereto by frequency modulating the ultrasonic pulses and filtering them. Then a good signal/noise ratio is obtained and better resolution in time. However, such an improvement means that, in the material measured, the speed of the pulses does not vary with the frequency. In any case, this improvement requires complex processing of the ultrasonic pulses, comprising self correlation and filtering. The result is that, when such processing is digitized, a large number of bits is required processed at a high frequency corresponding to the ultrasonic pulse generation rate. The digital processing device is therefore itself complex. In addition, to obtain ultrasonic pulses, it is necessary to apply high voltages to the electroacoustic transducers used (piezoelectric, ferroelectric, . . . ) which has drawbacks.

To overcome such drawbacks of known pulsed devices, alternating ultrasonic waves have already been used.

For example, the patent FR-A-2 476 831 describes a device comprising:

a generator generating a first alternating electric signal of fixed frequency;

an electroacoustic transmitting transducer able to convert said first alternating electric signal into an ultrasonic wave of the same fixed frequency, whose amplitude varies alternately as a function of time, said ultrasonic wave and said first electric signal being in a fixed phase relation;

first coupling means for applying said ultrasonic wave to said layer of material;

an electroacoustic receiving transducer capable of converting the ultrasonic wave which has passed through said layer of material into a second alternating electric signal in fixed phase relation with said wave;

second coupling means for applying, to said electroacoustic receiving transducer, said ultrasonic wave which has passed through said layer of material;

means for continuously measuring the variation of the phase-shift of said second electric signal with respect to to said first alternating electric signal applied to said measuring means; and computing means for deriving said variation of distance from said phase-shift variation.

Thus, according to this other known technique, an alternating ultrasonic wave is used continuously, which overcomes the drawback of the known pulsed technique, recalled above, due to the inaccuracy of the knowledge of the beginning of the ultrasonic pulses. In addition, because pulses are not used, the electric voltage applied to the transmitting transducer is not high. Such a technique using an alternating ultrasonic wave gives accurate, reliable measurements which do not require a high number of bits for the computations.

In known devices using this known technique with alternating ultrasonic wave, said layer of material is plunged into a bath of liquid able to transmit said wave and the electroacoustic transmitting and receiving transducers are disposed on each side of said layer of material. Thus, said first and second coupling means are formed by the thicknesses of said liquid between said electroacoustic transducers and the faces of said layer, respectively opposite said transducers.

The result is that such devices are inconvenient in use, since they require said layer of material to be plunged in a liquid bath. In addition, they cannot be used in all cases where it might be desirable to measure the variation of thickness of said layer, particularly when one of the faces of said layer is inaccessible, or when it is subjected to particularly difficult physical and chemical conditions, at the origin of said thickness variation. Moreover, with such a known arrangement, the device is formed with as many discrete devices as it comprises elements.

SUMMARY OF THE INVENTION

The object of the present invention is to overcome such drawbacks. It relates to a device of the above recalled type, which may be conveniently used, even when one of the faces of the layer to be examined is inaccessible or is subjected to difficult conditions (for example high temperatures), the structure of this device making it possible in addition to group some of the elements thereof together so as to form a probe easy to use.

For this, in accordance with the invention, the device of the above type using an alternating ultrasonic wave is remarkable in that:

said electroacoustic transmitting and receiving transducers, as well as said first and second coupling means are disposed on the same side of said layer of material; and said first and second coupling means are solid ultrasonic wave-guides.

Thus, the use of a liquid bath in which said layer of material is plunged can be avoided and, moreover, said variation of distance can be measured by approaching said layer from only one side, the other side being possibly inaccessible or affected by unfavorable conditions.

It will be noted that, in the device of the invention, the incident ultrasonic wave after passing through said layer of material in one direction is reflected from the opposite face of said layer of material, to pass again through this layer in the opposite direction and reach said electroacoustic receiving transducer.

It will be further noted that, in the device of the invention, it is easy to assemble said electroacoustic transmitting and receiving transducers together as well as said first and second coupling means in a case so as to form a unit which can be applied against a face of said layer of material.

Thus, the variation of thickness of said layer of material may be measured by applying said unit against an accessible face of this layer, even if the other face is subjected to high thermal conditions. It is useful to note that, because of the solid ultrasonic wave-guides, said electroacoustic transducers are distant from said layer of material, so that they are protected against the unfavorable thermic conditions which may exist at the same side as the inaccessible face of the layer of material. Of course, these wave-guides may for this purpose be made from a refractory material; they are for example formed by bars of such a refractory material. It can then be seen that said unit may form a probe.

Consequently, the present invention also relates to such a probe.

Thus, in accordance with the invention, the probe for measuring the variation of the distance separating the two faces of a layer of solid material by means of ultrasounds passing transversely through said layer is remarkable in that it comprises:

an electroacoustic transmitting transducer capable of converting a first alternating electric signal into an ultrasonic wave of the same fixed frequency, whose amplitude varies alternately as a function of time, said ultrasonic wave and said first electric signal being in a fixed phase relation;

a first rigid ultrasonic wave-guide, for applying said ultrasonic wave to said layer of material and disposed so that one of its ends is connected to said electroacoustic transmitting transducer whereas the other of its ends is free so as to be brought into contact with an accessible face of said layer of material;

an electroacoustic receiving transducer capable of converting the ultrasonic wave which has passed through said layer of material into a second alternating electric signal in fixed phase relation with said wave;

a second rigid ultrasonic wave-guide, intended to apply, to said electroacoustic receiving transducer, said ultrasonic wave which has passed through said layer of material and disposed so that one of its ends is connected to said electroacoustic receiving transducer, whereas the other of its ends is free so as to be brought, like the free end of the first wave-guide, into contact with said same accessible face of said layer of material;

first connection means for connecting said electroacoustic transmitting transducer to a generator generating said first alternating electric signal; and second connection means for connecting said electroacoustic receiving transducer to means able to measure continuously the variation of the phase-shift of said second electric signal with respect to said first electric signal.

Not only in the device, but also in the probe according to the invention, known transducers may be used of piezoelectric, ferroelectric or similar type, so that the first and second signals are in phase with the ultrasonic wave. Thus, particularly advantageous "fixed phase relations" are obtained. However, such an arrangement is not obligatory and the invention could be used with first and second signals phase-shifted with respect to the ultrasonic wave, provided that the corresponding phase-shifts are known.

Moreover, it is advantageous for said first alternating electric signal of fixed frequency to be of sinusoidal type. Furthermore, in order to make distance variation measurements greater than the wavelength of the ultrasonic wave (equal to the period of said first signal), means are provided for counting the passages through 2 k π of said phase-shift variation, k being an integer equal to 1, 2, 3, ... (n−1), n.

It will be noted that the invention may be used for measuring the variations of thickness of said layer of solid material, whatever the nature of this layer and whatever the procedure by which said thickness varies. This variation of thickness may result from abrasion or deposition on a face of said layer.

Advantageously, said probe comprises a case containing said electroacoustic transmitting and receiving transducers, as well as said first and second rigid ultrasonic wave-guides, the case having said first and second connection means passing therethrough. In this instance, the free ends of said rigid ultrasonic waveguides, opposite said electroacoustic transmitting and receiving transducers, are accessible outside said case, so as to be coupled to said same accessible face of said layer of material.

Coupling between said free ends of said rigid ultrasonic wave-guides to said same accessible face of said layer of material may be obtained by simple contact. However, preferably, temporary fastening means of said free ends on said same accessible face is provided, for example using a cement. If said layer of material is subjected, on its face opposite said same accessible face, to high temperatures, said fastening means may be made using a refractory cement.

Such temporary fastening means provides good transmission of the ultrasonic wave between said rigid ultrasonic wave-guides and said layer of material.

To further increase the quality of the ultrasonic coupling between the probe and the layer of material to be examined, the following features may be provided, alone but preferably in combination:

said case comprises an end able to come into contact with said same accessible face of the layer of material, when said accessible free ends of said rigid ultrasonic wave-guides are coupled to said same accessible face and, in addition, said electroacoustic transmitting and receiving transducers are in contact with said case;

fixing means are provided for fixing said end of said case on said same accessible face of the layer of material;

said electroacoustic transmitting and receiving transducers, as well as said first and second rigid ultrasonic wave-guides are embedded, inside said case, in a mass of material absorbing the ultrasonic waves.

This last feature ensures great rigidity between the different elements of the probe, while avoiding parasite coupling between the transmitting side and the receiving side thereof.

It is advantageous for said free accessible ends of said rigid ultrasonic wave-guides to project outside said mass of material absorbing the ultrasonic waves, this mass forming a free space between its front and said same accessible face of the layer of material. Thus, a buffer space is obtained between said layer of material and the inside of the probe, particularly useful when the probe is used for examining a layer of material subjected to high temperatures on its face opposite the probe. In this instance, it is advantageous for the mass of material absorbing the ultrasonic waves, as well as said ultrasonic wave-guides to be made from refractory material. To protect said electroacoustic transmitting and receiving transducers as much as possible from the high temperatures, it is then preferable to dispose them inside said case in the vicinity of the end thereof opposite said end coming into contact with said same accessible face of the layer of material.

BRIEF DESCRIPTION OF THE DRAWINGS

The figures of the accompanying drawings will better show how the invention may be put into practice. In these figures, identical references designate similar elements.

DESCRIPTION OF THE PREFERRED EMBODIMENT

Figure 1:
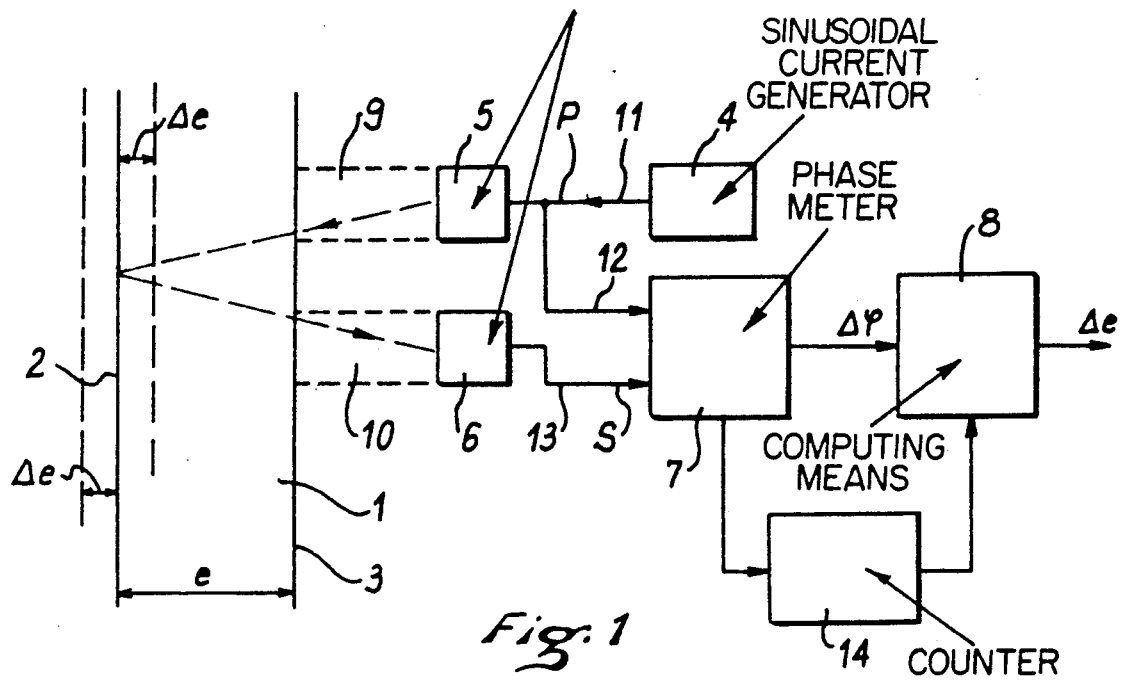
FIG. 1 is the block diagram of one embodiment of the device according to the invention.

The device according to the invention, illustrated schematically in FIG. 1, is intended to measure the variation $\Delta e$ of the thickness e of a layer of solid material 1, defined by two opposite faces 2 and 3. For example, the variation of thickness $\Delta e$ may result from a deposition on the layer of solid material 1 (thickness e increases) or else wearing of said layer (then the thickness e decreases).

Furthermore, this variation of thickness results from the evolution of a single one 2 of said faces with respect to an initial position, the other 3 of said faces being invariable.

The system of FIG. 1 comprises a sinusoidal current generator 4, two electroacoustic transducers 5 and 6, for example of piezoelectric or ferroelectric type, a phasemeter 7 or similar and computing means 8.

The electroacoustic transducers 5 and 6 are disposed on the same side as the invariable face 3 of the layer of solid material 1, close to each other. Transducer 5 is coupled acoustically to said invariable face 3 by a solid wave-guide 9. Similarly, the acoustic coupling between transducer 6 and face 3 is provided by a solid wave-guide 10.

Figure 2A:
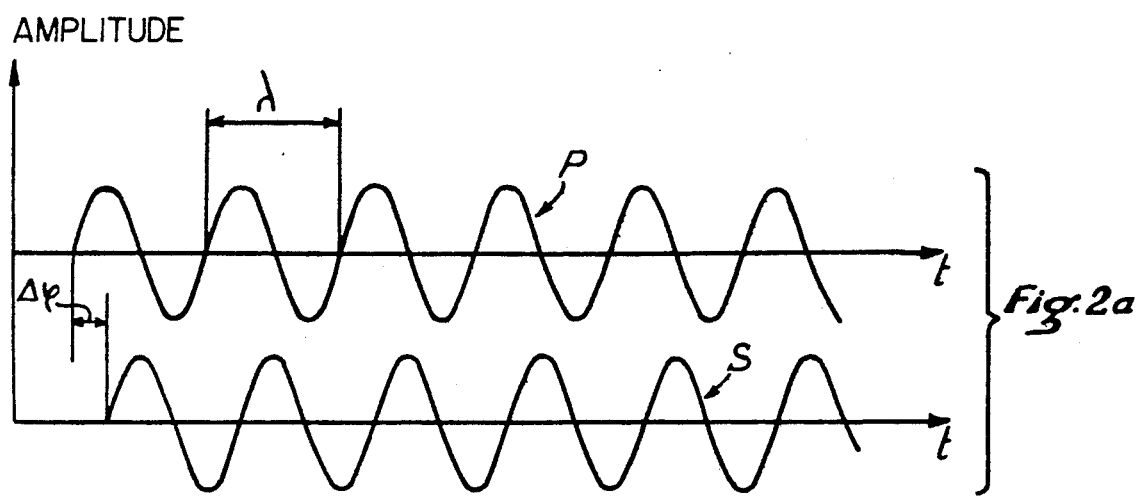
FIGS. 2a, 2b and 2c are timing diagrams illustrating the operation of the device of FIG. 1.
Figure 2B:
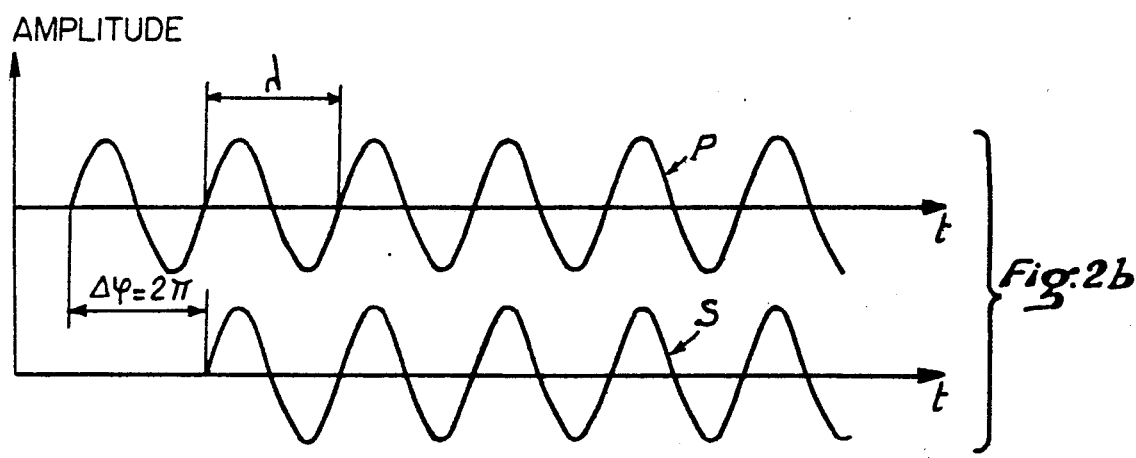

The sinusoidal electric signal p of period $\lambda$, emitted by generator 4 is applied by connection 11 to transducer 5. In response to such energization, transducer 5 emits a sinusoidal ultrasonic wave of frequency $1/\lambda$, in phase with said electric signal P. Via the wave-guide 9, this sinusoidal ultrasonic wave is applied, by face 3, to the layer of material 1 which it passes through and is reflected from the face 3, so that it is caused to pass again through the layer of material 1 in the reverse direction, towards the wave-guide 10. During this double passage through the layer of material 1, the ultrasonic wave undergoes a phase-shift which is proportional to the thickness e passed through twice. Consequently, the ultrasonic wave transmitted by the wave-guide 10 to the receiving transducer 6 is phase-shifted with respect to the ultrasonic wave generated by transducer 5 by an angle $$\phi = 2k \cdot e \qquad (1)$$

k being a constant equal to the wave number $\pi\lambda$. In fact a phase-shift $\phi$ equal to $2\pi$ corresponds to a thickness $2e$ equal to $\lambda$ (see FIG. 2b).

Transducer 6, receiving the ultrasonic wave which has passed through layer 1, emits a sinusoidal electric signal S of period $\lambda$ in phase with this ultrasonic wave which it receives. The result is that the sinusoidal electric signal S emitted by the receiving transducer 6 is phase-shifted by $\phi$ with respect to the sinusoidal electric signal P emitted by generator 4.

Thus, the phase-shift of signal S with respect to signal P (see FIG. 2a) is representative of twice the thickness e of layer 1.

If the thickness e varies by a small amount $\Delta e$ (more or less), the result is a phase-shift variation $\Delta\phi$ such that:

$$\Delta\phi = 4\pi/\lambda \cdot \Delta e \qquad (2)$$

To obtain this value $\Delta\phi$, in the system of FIG. 1, the signals P and S are applied respectively by connections 12 and 13 to the phasemeter 7, which delivers the corresponding phase-shift variation at its output. The computing means 8 receiving this phase-shift variation calculate the corresponding thickness variation $\Delta e$ by the formula:

$$\Delta e = \lambda/4\pi \cdot \Delta\phi \qquad (3)$$

The thickness variation $\Delta e$ is therefore available at the output of said computing means 8.

Figure 2C:
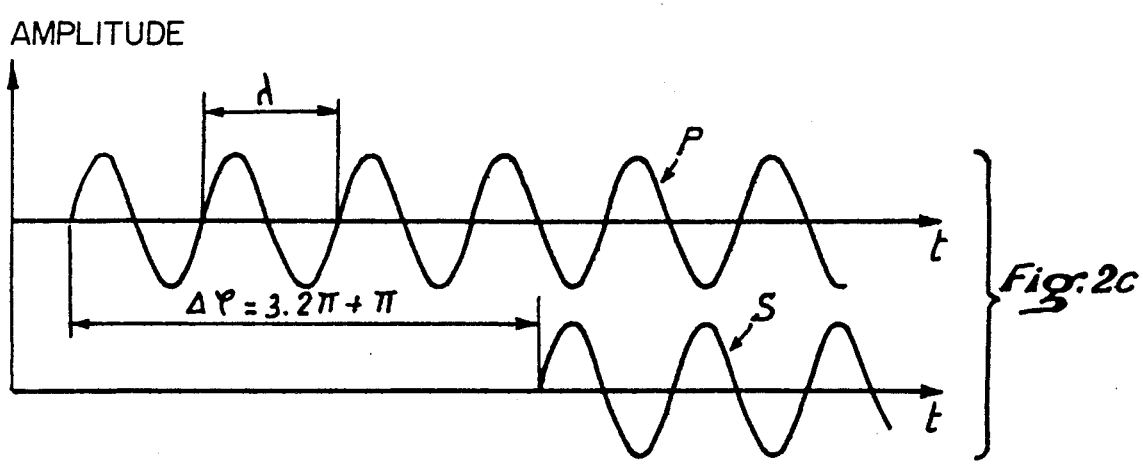

It is clear from the foregoing that the present invention has numerous advantages:

a) measurement of the thickness variation $\Delta e$ is very accurate and depends only on the accuracy of the measurement of $\Delta\phi$. If, for example, the accuracy of measurement of $\Delta\phi$ is equal to 1°, then the accuracy of measuring $\Delta e$ is $\lambda/360$. If the accuracy of measurement of $\Delta\phi$ is 0.1°, that of $\Delta e$ is equal to $\lambda/3600$. The wavelength $\lambda$ being for example chosen between 5 mm and 20 mm, it can then be seen that the accuracy in determining $\Delta e$ may be within a few microns.

b) the dynamics of the measurement are very great for the variation $\Delta e$ may be as high as desired, whatever the value of $\lambda$. It is sufficient for the phasemeter 7 (or external counting means 14) to record the passages of $\Delta\phi$ through $2k\pi$. For example (see FIG. 2C) if, with a value of $\lambda$ equal to 10 mm, a phase-shift variation $\Delta\phi$ is measured equal to three times $2\pi$ increased by $\pi$, that means that:

$$\Delta e = \frac{\lambda}{4\pi}(3.2\pi + \pi) = \frac{7\lambda}{4} = 17.5 \text{ mm}$$

The variation $\Delta e$ may then be greater than $\lambda$.

c) the measurement may be digitized with a relatively low number of bits, since it is sufficient, for each measurement, to code the phase difference $\Delta\phi$ and the number k representing the passages through $2k\pi$ of $\Delta\phi$. There is no bit to be provided for ancillary signal processing, such as self correlation, filtering, etc. . . .

d) linearity of the measurement is provided because of operating at a fixed frequency.

Figure 3:
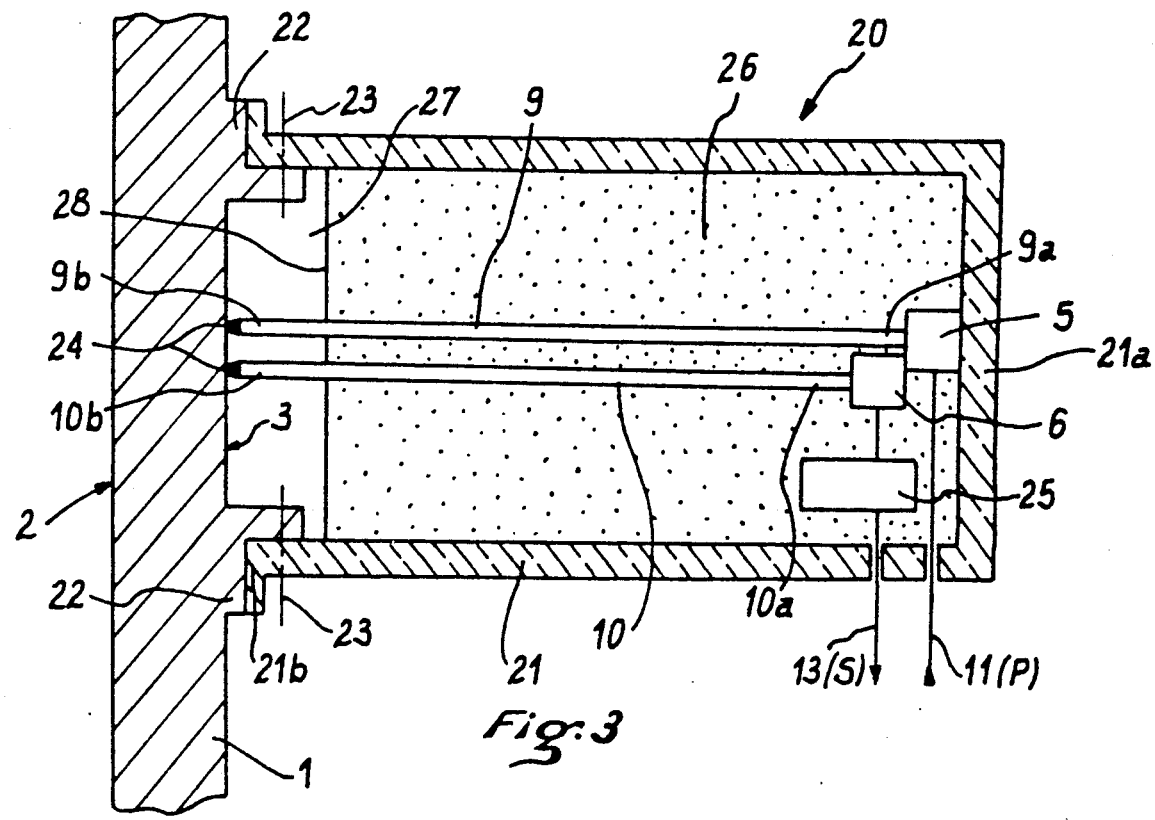
FIG. 3 shows schematically one embodiment of a probe for the device of the invention.

In FIG. 3, a practical embodiment 20 has been shown of a probe for the device of FIG. 1, for example for measuring the recession by thermal ablation of the external face 2 of layer 1. This layer 1 may for example be the wall of the nose of a space shuttle when it re-enters the atmosphere. Such a nose is made for example from a thermomechanical material with ablative structure (for example a carbon/carbon material whose thickness is about 10 mm). The ablation measurements are made during experimental tests in flight and allow the calculations of the resistance of the material at high temperatures to be checked. Such thickness measurements of wall 1 of the nose are difficult to carry out in a disturbed environment. In fact, the temperature on the external face 2 of wall 1 may rise to 2000° C.

As can be seen, probe 20 according to the invention comprises the above mentioned elements 5, 6, 9 and 10 enclosed in a case 21 intended to be fixed on the invariable internal face 3 of wall 1 of the nose of the space shuttle. For this, reinforcements 22 are provided in said wall.

Said case 21 has the form of a cylinder closed at one of its ends by a bottom 21a and open at its other end 21b, for fixing to the wall 1. The transducers 5 and 6 are disposed close to the bottom 21a (distant from wall 1) of said case 21 and are connected to the corresponding respective ends 9a and 10a of the wave-guides 9 and 10. The opposite ends 9b and 10b of said wave-guides, intended to be coupled to the wall 1, are accessible in the opening of case 21.

For the above application, case 21 must:

withstand high temperatures (of the order of 1500° C. on the internal invariable face 3 of the nose of the shuttle), withstand considerable vibrations and in a difficult dynamic context, have minimum weight.

To satisfy these criteria, case 21 is for example made by machining from a cylindrical block of composite material, comprising a woven framework in three dimensions from silica fibers and a phenol resin matrix. The thickness of the wall of case 21 is for example between 4 and 8 mm and its inner diameter may be about 50 mm.

Fixing screws, represented simply by their axes 23 and made from a thermostructural material of the composite ceramic type (SiC/SiAl YoN or $SiC/Si_3N4$), are provided for fixing case 21 on reinforcements 22.

Considering the thermal environment of such a probe, it is necessary to decouple the transducers 5 and 6 thermally from wall 1. This is obtained by the fact that the two ultrasonic transducers 5 and 6 are connected to the internal invariable face 3 of wall 1 via wave-guides 9 and 10, made for this purpose from a refractory material transparent to the acoustic waves, for example from silica, alumina, or tungsten.

The two wave-guides 9 and 10, arranged substantially parallel to each other, are coupled to the internal invariable face 3 of wall 1 of the nose by temporary fastening means of refractory cement 24, which provides excellent acoustic coupling between said wall 1 and ends 9b and 10b of said wave-guides.

The length of the wave-guides 9 and 10 is calculated and determined so as to limit the temperature to less than 300° C. at the level of transducers 5 and 6. This length, for the above application, may be about 100 mm, and it is related:

to the thermal flux, and the thermal conductivity of the material of said wave-guides.

Each wave-guide 9 and 10 may be in the form of a solid cylindrical bar made from silica, alumina or any other refractory material transparent to the acoustic waves. Its diameter, for example 2 mm, must be compatible with the ultrasonic wavelength used (for example 10 mm).

The mechanical connection between wave-guides 9 and 10 and wall 2, provided by refractory cement fastening means 24, is completed by case 21, fixed to said wall by its end 21b, bearing against transducers 5 and 6, which provides additional mechanical strength by stacking.

The two transducers 5 and 6 are positioned so that their two acoustic axes are offset by at most 4 to 5 mm, so as to improve the efficiency of the reception of the ultrasonic wave at the level of the end of the acoustic wave-guides.

The receiving transducer 6 may be connected to a block 25 comprising a pre-amplifier, which may be integrated in case 21. The electric connections 11 and 13, to the generator 4 and to the phasemeter 7 outside case 21, pass through said case and are isolated by refractory silica sheaths (not shown) withstanding temperatures which may reach 300° C. in the zone of said transducers.

Each transducer 5, 6 may be coupled acoustically and mechanically to the corresponding wave-guide 9, 10 by bonding to the respective end 9a, 10a.

The assembly formed by the wave-guides 9, 10, transducers 5, 6 and possibly the pre-amplifier 15 is molded from a block of refractory foam 26 injected inside case 21 and intended to absorb the vibrations. Furthermore, the pores of this foam provide acoustic decoupling between the two wave-guides 9, 10, thus avoiding any risks of cross interference between the transmitting part and the receiving part of probe 20.

Filling of case 21 with the refractory foam 26 is not complete so as to leave a space 27 between the front 28 of the foam block 26 and the invariable internal face 3 of wall 1. This space 27, forming an insulating chamber, depends on the characteristics of the foam used, on the thermal propagation law and on the flight time of the shuttle. For example, for a refractory foam made from sintered wool (quartz-silica), space 27 is such that the distance between the internal face 3 and the front 28 is about 10 mm.

What is claimed is:

1. Probe for measuring the variation of the distance separating the two faces of a layer of solid material by means of ultrasounds passing transversely through said layer, comprising:

an electroacoustic transmitting transducer capable of converting a first alternating electric signal into an ultrasonic wave of the same fixed frequency, whose amplitude varies alternately as a function of time, said ultrasonic wave and said first electric signal being in a fixed phase relation;

a first rigid ultrasonic wave-guide, for applying said ultrasonic wave to said layer of material and disposed so that one of its ends is connected to said electroacoustic transmitting transducer whereas the other of its ends is free so as to be brought into contact with an accessible face of said layer of material;

an electroacoustic receiving transducer capable of converting the ultrasonic wave which has passed through said layer of material into a second alternating electric signal in fixed phase relation with said wave;

a second rigid ultrasonic wave-guide, intended to apply, to said electroacoustic receiving transducer, said ultrasonic wave which has passed through said layer of material and disposed so that one of its ends is connected to said electroacoustic receiving transducer, whereas the other of its ends is free so as to be brought, like the free end of the first wave-guide, in contact with the same accessible face of said layer of material;

first connection means for connecting said electroacoustic transmitting transducer to a generator generating said first alternating electric signal;

second connection means for connecting said electroacoustic receiving transducer to means able to measure continuously the variation of the phase-shift of said second electric signal with respect to said first electric signal;

a case containing said electroacoustic transmitting and receiving transducers as well as said first and second rigid ultrasonic wave-guides, the case having said first and second connection means passing therethrough;

the free ends of said rigid ultrasonic wave-guides, opposite said electroacoustic transmitting and receiving transducers, being accessible outside said case for coupling to said same accessible face of said layer of material.

2. The probe as claimed in claim 1, wherein said first alternating electric signal generated by said generator is sinusoidal.

3. The probe as claimed in claim 1, further comprising means for counting the passages through $2k\pi$ of said phase-shift variation, k being an integer equal to 1, 2, 3, ..., (n−1), n.

4. The probe as claimed in claim 1, wherein coupling between said free ends of said rigid wave-guides and said same accessible face of said layer of material comprises temporary fastening means of aid ends on said same accessible face.

5. The probe as claimed in claim 1, wherein said case comprises an end able to come into contact with said same accessible face of the layer of material, when said accessible free ends of said rigid ultrasonic wave-guides are coupled to said same accessible face and said electroacoustic transmitting and receiving transducers are in contact with said case.

6. The probe as claimed in claim 5, further comprising fixing means for fixing said end of said case on said same accessible face of the layer of material.

7. The probe as claimed in claim 1, wherein said electroacoustic transmitting and receiving transducers, as well as said first and second rigid ultrasonic wave-guides are embedded, inside said case, in a mass of material absorbing the ultrasonic waves.

8. The probe as claimed in claim 7, said free accessible ends of said rigid ultrasonic wave-guides project outside said mass of material absorbing the ultrasonic waves, this mass forming a free space between its front and said same accessible face of the layer of material.

9. The probe as claimed in claim 7, wherein said mass of material absorbing the ultrasonic waves, as well as said ultrasonic wave-guides are made from refractory material.

10. The probe as claimed in claim 1, wherein said electroacoustic transmitting and receiving transducers are disposed inside said case in the vicinity of the end thereof opposite said end coming into contact with said same accessible face of the layer of material.

* * * * *

UNITED STATES PATENT AND TRADEMARK OFFICE
CERTIFICATE OF CORRECTION

PATENT NO. : 5,052,227

DATED : October 1, 1991

INVENTOR(S) : CHRISTIAN MARCEL LeFLOC'H ET AL.

It is certified that error appears in the above-identified patent and that said Letters Patent is hereby corrected as shown below:

On the title page, item [73] Assignee: "Societe Nationale Industrielle" should be --Aerospatiale Societe Nationale Industrielle--.

Signed and Sealed this

Twenty-eighth Day of June, 1994

Attest:

BRUCE LEHMAN

*Attesting Officer*    *Commissioner of Patents and Trademarks*